United States Patent
Selwood

(10) Patent No.: US 9,682,924 B2
(45) Date of Patent: Jun. 20, 2017

(54) CRYSTALLINE FORM OF VSN16

(71) Applicant: CANBEX THERAPEUTICS LIMITED, London (GB)

(72) Inventor: David Selwood, London (GB)

(73) Assignee: CANBEX THERAPEUTICS LIMITED, Greater London (GB)

( * ) Notice: Subject to any disclaimer, the term of this patent is extended or adjusted under 35 U.S.C. 154(b) by 0 days.

(21) Appl. No.: 14/760,592

(22) PCT Filed: Jan. 17, 2014

(86) PCT No.: PCT/GB2014/050127
§ 371 (c)(1),
(2) Date: Jul. 13, 2015

(87) PCT Pub. No.: WO2014/111720
PCT Pub. Date: Jul. 24, 2014

(65) Prior Publication Data
US 2015/0353476 A1 Dec. 10, 2015

(30) Foreign Application Priority Data
Jan. 18, 2013 (GB) .................................. 1300903.0

(51) Int. Cl.
*C07C 233/69* (2006.01)

(52) U.S. Cl.
CPC ........ *C07C 233/69* (2013.01); *C07B 2200/13* (2013.01)

(58) Field of Classification Search
USPC ................................. 514/620; 564/156, 164
See application file for complete search history.

(56) References Cited

U.S. PATENT DOCUMENTS

| 7,696,382 B2 * | 4/2010 | Okuyama | ................ | C07C 69/76 |
| | | | | 558/388 |
| 2013/0123356 A1 * | 5/2013 | Okuyama | ................ | C07C 69/76 |
| | | | | 514/521 |

FOREIGN PATENT DOCUMENTS

| WO | 2005/080316 A2 | 9/2005 |
| WO | 2010/116116 A1 | 10/2010 |

OTHER PUBLICATIONS

Gennaro A R (editor), Remington's Pharmaceutical Sciences, 1985, 17th Edition, Mack Publishing Co, Bibliographic Information and Table of Contents.

Hoi P M et al., "Vascular pharmacology of a novel cannabinoid-like compound, 3-(5-dimethylcarbamoyl-pent-1-enyl)-N-(2-hydroxy-1-methyl-ethyl)benzamide (VSN16) in the rat," British Journal of Pharmacology, 2007, 152, pp. 751-764.
Hopper AT et al., "Design, Synthesis, and Biological Evaluation of Conformationally Constrained aci-Reductone Mimics of Arachidonic Acid," Journal of Medicial Chemistry, 1998, vol. 41 p. 420-427.
Hoye R C et al., "Synthesis of Elenic Acid, an Inhibitor of Topoisomerase II," Journal of Organic Chemistry, 1999, 64, pp. 2450-2453.
Wade W & Weller PJ (editors), Handbook of Pharmaceutical Excipients, 1994, 2nd edition, The Pharmaceutical Press, Bibliographic Information.
Caira, M. R. "Crystalline Polymorphism of Organic Compounds," Topics in Current Chemistry, v198, 1998, p. 163-208, dated Jan. 1, 1998.
International Preliminary Report on Patentability for International Patent Application No. PCT/GB2014/050127, dated Jul. 21, 2015.
International Search Report for International Patent Application No. PCT/GB2014/050127, dated Aug. 4, 2014.
Written Opinion of the International Searching Authority for International Patent Application No. PCT/GB2014/050127, dated Aug. 4, 2014.
Zhu et al. (2007) Microscale Experiment of Organic Chemistry. 2nd Ed. Chemical Industry Press. Beijing, China. p. 34.—with English translation.

* cited by examiner

*Primary Examiner* — Pancham Bakshi
(74) *Attorney, Agent, or Firm* — Lathrop & Gage LLP; Brian C. Trinque

(57) ABSTRACT

The present invention relates to a compound of formula (I) in crystalline form, wherein said compound is in the form of the free base or a pharmaceutically acceptable salt thereof, or a solvate of the free base or salt form thereof. The invention also relates to a pharmaceutical composition containing said crystalline form as an active ingredient, and use thereof in the prevention or treatment of disease. The invention further relates to a process for preparing the crystalline form.

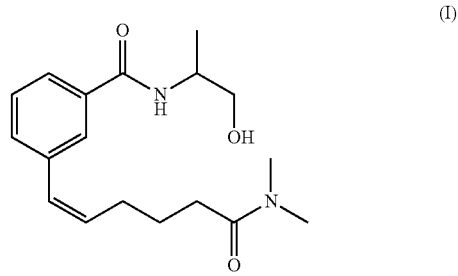

(I)

7 Claims, 3 Drawing Sheets

CRYSTALLINE FORM OF VSN16

RELATED APPLICATIONS

This application is a 35 U.S.C. §371 filing of International Application No. PCT/GB2014/050127, filed Jan. 17, 2014, which claims priority to Great Britain Patent Application No. 1300903.0, filed Jan. 18, 2013, each of which are incorporated herein by reference in their entireties.

The present invention relates to crystalline forms of a compound therapeutically useful in the treatment of muscular disorders, gastrointestinal disorders, or for controlling spasticity or tremors.

BACKGROUND TO THE INVENTION

WO 2005/080316 (in the name of University College London) discloses compounds capable of modulating cannabinoid or cannabinoid-like receptors, including VSN16, the structure of which is shown below.

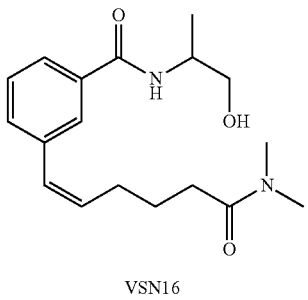 [SMILES: CC(CO)NC(=O)c1cccc(/C=C\CCCC(=O)N(C)C)c1 ; "VSN16"]

VSN16

Initial studies demonstrated that VSN16 and related compounds exhibited a marked effect on spasticity in CREAE mice, providing strong evidence that a selective inhibition of spasticity was achieved without producing significant adverse CNS effects. Studies also demonstrated that the compounds inhibited gastrointestinal motility, as measured using a colonic propulsion test. VSN16 is understood to act on the endothelium to release nitric oxide and activate $K_{Ca}$ and $TRPV_1$. Its solubility is believed to play a significant role in bringing about peripheral cannabinoid-like effects without accompanying central or severe cardiovascular responses.

WO 2005/080316 discloses the preparation of VSN16 as shown in Scheme 1 below.

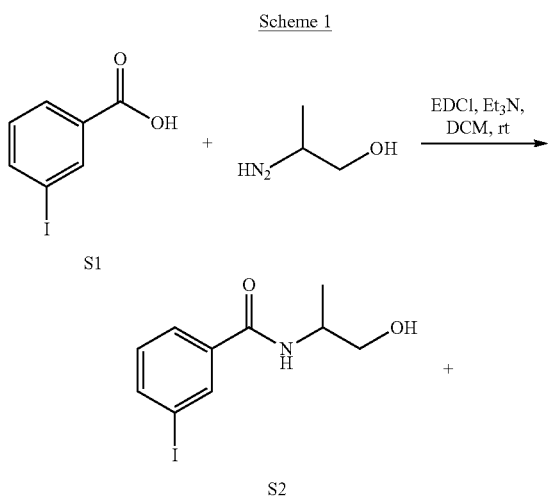

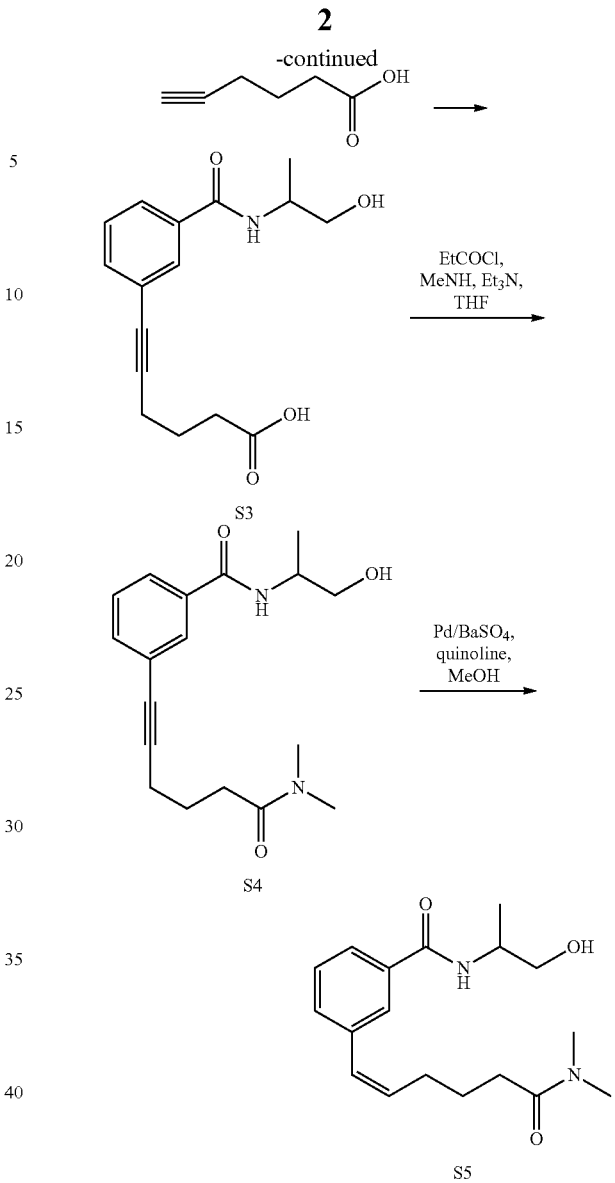

A palladium catalysed Songashira coupling reaction was used to insert a variety of alkyl side chains into 3-iodo methyl benzoate. The target compounds (S5) and related analogues were synthesised by a simple four-step route. First, the acid (S1) was reacted with DL alaninol in the presence of a diimide (EDCI) to give the amide (S2) in good yield. Palladium-catalysed coupling [Hoye, R. C. et al, *J. Org. Chem.* 1999, 64, 2450-2453; Hopper, A. T. et al, *J. Med. Chem.* 1998, 41, 420-427] of the amide with the alkyne acid in the presence of $Cu^I I$ and pyrrolidine proceeded smoothly to give the alkyne (S3). The acid (S3) was quantitatively transformed into (S4) using ethylchloroformate and dimethylamine HCl. Lindlar catalysed reduction yielded the target alkene (S5). Alternatively, (S4) can be reduced with borohydride (polymer supported), $(CH_3COO)_2Ni.4H_2O$, MeOH, and $H_2$ at atmospheric pressure (P. M. Hoi, C. Visintin, M. Okuyama, S. M. Gardiner, T. Bennett, D. Baker, D. L. Selwood and C. R. Hiley; *British Journal of Pharmacology,* 2007, 1-14). The flexibility of this method allows the synthesis of a large number of different compounds using a range of alkynes for the Sonogashira coupling, or by starting with a different amine for the amide formation in the first step. However, the main drawback of this synthetic route is that the Lindlar catalytic reduction of intermediate (S4) yields a mixture of E- and Z-isomers of the resulting alkenyl compounds, requiring separation by reverse phase HPLC. This technique is both costly and time consuming, thereby rendering the method unsuitable for large scale synthesis.

More recently, WO 2010/116116 (UCL Business PLC) disclosed an alternative process for preparing VSN16 and related compounds. Specifically, WO 2010/116116 disclosed the preparation of VSN16 by the process set forth in Scheme 2 below, which comprises the steps of:
treating a compound of formula IV.1 with a compound of formula V.1 to form a compound of formula IIIb.1;
treating said compound of formula IIIb.1 with a compound of formula IIb.1, where PG is a protecting group, to form a compound of formula Ib.1; and
removing protecting group PG from said compound of formula Ib.1 to form VSN16 to provide crystalline forms of the compound VSN16 that exhibit one or more improved properties.

STATEMENT OF INVENTION

A first aspect of the invention relates to a crystalline form of the compound of formula (I)

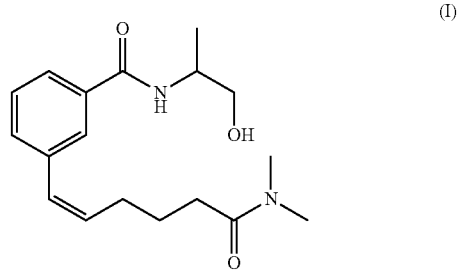 [SMILES: CC(CO)NC(=O)c1cccc(/C=C\CCCC(=O)N(C)C)c1]

wherein said compound is in the form of the free base or a pharmaceutically acceptable salt thereof, or a solvate of the free base or salt form thereof.

Scheme 2

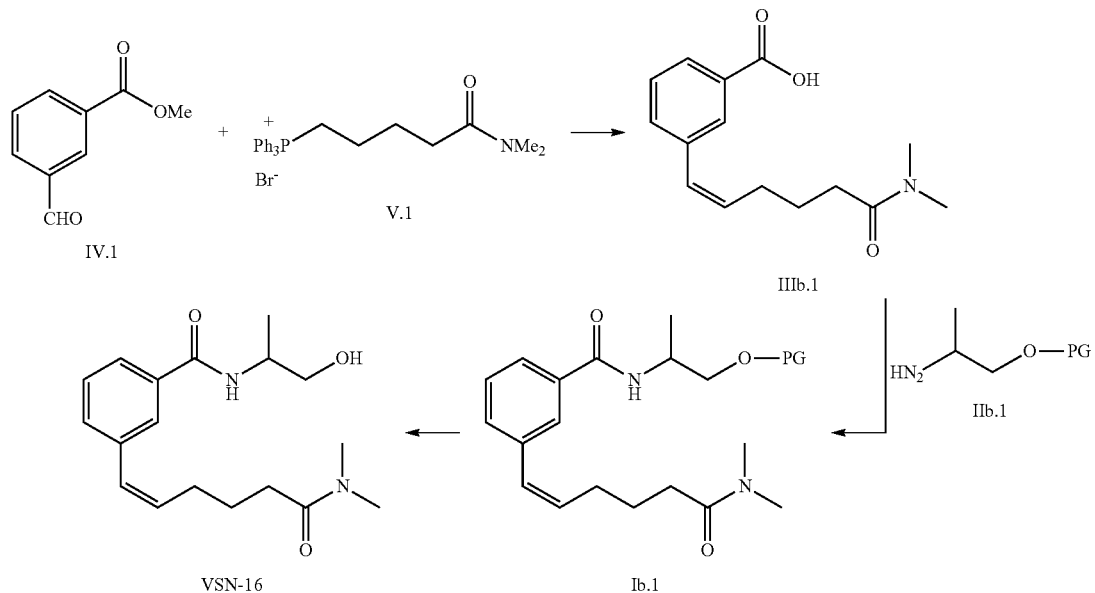

Advantageously, compound IIIb.1 can be separated from the corresponding Z isomer by crystallisation. This avoids the need for costly and time consuming purification using reverse phase HPLC, as required by previously described processes for preparing VSN16 and analogues thereof. Moreover, the ability to separate the E- and Z-isomers by crystallisation renders the process suitable for scale-up and contributes to an improved overall yield.

VSN16 prepared in accordance with the prior art methods described above is in the form of an oil. Ideally, for large scale preparation and purification purposes, it would be advantageous if VSN16 could be processed as a solid.

Accordingly, the present invention seeks to provide the compound VSN16 in crystalline form. In particular, the invention seeks to provide crystalline forms that retain the desired pharmacological activity of the compound. More specifically, but not exclusively, the present invention seeks The crystalline forms of the invention typically demonstrate one or more improved properties over the prior art forms. Suitable properties include, for example, one or more of the following: better storage stability, improved purity, improved ease of handling (flowability, compressibility, stability), easier purification, and easier synthetic scale up.

A second aspect of the invention relates to a pharmaceutical composition comprising a crystalline form as described above as an active ingredient and a pharmaceutically acceptable diluent, excipient or carrier.

A third aspect of the invention relates to a crystalline form as described above for use in medicine.

A fourth aspect of the invention relates to a crystalline form as described above for use in the prevention or treatment of a muscular disorder, a gastrointestinal disorder, or for treating or controlling spasticity and tremors.

A fifth aspect of the invention relates to use of a crystalline form as described above in the preparation of a medicament for the prevention or treatment of a muscular disorder, a gastrointestinal disorder, or for treating or controlling spasticity and tremors.

A sixth aspect of the invention relates to a method for the prevention or treatment of a muscular disorder, a gastrointestinal disorder, or for treating or controlling spasticity and tremors, said method comprising administering a pharmacologically effective amount of a crystalline form as described above to a subject in need thereof.

A seventh aspect of the invention relates to processes for preparing crystalline forms as described above.

DETAILED DESCRIPTION

The crystalline forms of the invention may be characterised by a range of different analytical techniques, including x-ray powder diffraction and differential scanning calorimetry. Further details of these techniques and equipment are set forth in the accompanying examples section.

As used herein, the term "solvate" or "solvated form" refers to a crystal having one or more molecules of solvent associated therewith as an inherent part of the crystal structure. Preferably, the solvate or solvated form is the hydrate.

In general, different plural crystalline forms (polymorphs) of the same compound can be produced by varying the crystallisation conditions used. These different crystalline forms have different three-dimensional structures and different physicochemical properties. However, the existence of polymorphs is inherently unpredictable and theoretical calculations to predict polymorphs are extremely unreliable, with many more polymorphs predicted than can actually be isolated in practice.

Preferably, the crystalline forms of the invention are at least 95% pure (in terms of the purity of the crystal form), more preferably, at least 97% pure, even more preferably, at least 98 or 99% pure (for example, as analysed by HPLC). More preferably still, the crystalline forms of the invention are at least 99.5% pure.

In one preferred embodiment of the invention, the crystalline form is of formula (Ia),

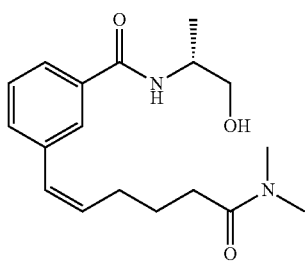

(Ia)

The present invention encompasses the crystalline form of the free base of compound (Ia) as well as crystalline forms of various pharmaceutically acceptable salts thereof.

One preferred embodiment of the invention relates to the crystalline form of the free base of compound (Ia).

Preferably, the crystalline form is characterized is characterized by an x-ray powder diffraction pattern having at least two diffraction peaks selected from the following 2[theta] values: 9.53±0.3, 10.35±0.3, 14.21±0.3, 14.35±0.3, 19.02±0.3, 19.18±0.3, 20.11±0.3, 20.34±0.3, 20.63±0.3, 21.55±0.3, 23.91±0.3, 24.03±0.3, 33.89±0.3, 38.48±0.3, 38.71±0.3, 38.89±0.3, 41.83±0.3 and 41.95±0.3.

More preferably, the crystalline form is characterized by having at least three, at least four, at least five, or at least six of the aforementioned diffraction peaks. Even more preferably, the crystalline form is characterized by having at least seven, eight, nine, ten, eleven, twelve, thirteen, fourteen, fifteen, sixteen, or seventeen of the aforementioned diffraction peaks.

In a more preferred embodiment, the crystalline form is characterized by having two, three, four, five, six, seven, eight, nine, ten, eleven, twelve, thirteen, fourteen, fifteen, sixteen, seventeen or eighteen of the aforementioned diffraction peaks.

Even more preferably, the crystalline form is characterized by an x-ray powder diffraction pattern having at least two diffraction peaks selected from the following 2[theta] values: 9.53±0.3, 14.21±0.3, 14.35±0.3, 19.02±0.3, 19.18±0.3, 20.34±0.3, 21.55±0.3, 38.71±0.3 and 38.89±0.3.

More preferably, the crystalline form is characterized by having at least three, at least four, at least five, or at least six of the aforementioned diffraction peaks. Even more preferably, the crystalline form is characterized by having at least seven or eight of the aforementioned diffraction peaks.

In a more preferred embodiment, the crystalline form is characterized by having two, three, four, five, six, seven, eight or nine of the aforementioned diffraction peaks.

In a more preferred embodiment, the crystalline form is characterized by an x-ray powder diffraction pattern having at least two diffraction peaks selected from the following 2[theta] values: 9.53±0.3, 14.21±0.3, 14.35±0.3, 38.71±0.3 and 38.89±0.3.

More preferably, the crystalline form is characterized by having at least three or at least four of the aforementioned diffraction peaks.

In a more preferred embodiment, the crystalline form is characterized by having two, three or four or five of the aforementioned diffraction peaks.

In one highly preferred embodiment, the crystalline form is characterized by an x-ray powder diffraction pattern in which the peak positions are substantially in accordance with the peak positions of the pattern shown in FIG. 1 or listed in Table 1.

A further aspect of the invention relates to a process for preparing a crystalline compound of formula (Ia), said process comprising the steps of:
(i) dissolving a compound of formula (Ia) in a solvent selected from methyl acetate and ethyl acetate in a reaction vessel to form a solution;
(ii) removing the solvent by rotary evaporation to give an oil;
(iii) optionally repeating steps (i) and (ii) one or more times;
(iv) scratching the reaction vessel with a glass rod to induce crystallization; and
(v) leaving the oil to crystallize.

In one preferred embodiment, steps (i) and (ii) are repeated once or twice, more preferably once.

In one preferred embodiment, step (v) comprises leaving the oil at room temperature until crystallization occurs.

In one preferred embodiment, step (v) comprises leaving the leaving the oil at room temperature for a period of at least 24 hours, more preferably, at least 48 hours, even more preferably, at least 72 hours, even more preferably still, at least a week.

In one preferred embodiment step (v) comprises leaving the oil at a temperature from about 10° C. to about 30° C., more preferably, about 15° C. to about 25° C., more preferably, about 20° C. to about 25° C.

A further aspect of the invention relates to a process for preparing a crystalline compound of formula (Ia), said process comprising the steps of:
(i) dissolving a compound of formula (Ia) in a solvent selected from methyl acetate or ethyl acetate to form a solution;
(ii) cooling the solution obtained in step (i) to a temperature of less than about 5° C.;
(iii) adding one or more seed crystals of said compound of formula (Ia) to the solution and stirring the mixture so produced;
(iv) isolating the crystalline material formed in step (iii);
(v) optionally repeating steps (i) to (iv).

In one preferred embodiment, step (i) comprises warming the mixture to form a solution. Preferably, step (i) comprises warming the mixture to a temperature of at least 40° C., more preferably, at least 45° C., even more preferably, at least 50° C.

In one preferred embodiment, step (i) comprises cooling the solution obtained in step (i) to a temperature of about 0° C., even more preferably, to a temperature of less than about 0° C.

In one preferred embodiment, step (ii) comprises isolating the crystalline material by filtration.

In one preferred embodiment, step (iii) comprises stirring the mixture for a period of at least 1 hour, more preferably, at least 2 hours or 3 hours.

In one preferred embodiment, step (iv) further comprises washing the crystalline material with cold solvent, wherein the solvent is the same solvent used in step (i). Preferably, the isolated material is dried in vacuo until constant mass is achieved. More preferably, the isolated material is dried in vacuo at a temperature of about 25° C.

In one highly preferred embodiment, the solvent is methyl acetate.

In one preferred embodiment, steps (i) to (iv) are repeated. If necessary, and in a preferred embodiment, before repeating steps (i) to (iv), the material is dissolved in an organic solvent (e.g. dichloromethane) and washed at least once with an aqueous acid solution (e.g. 0.1M HCl solution). The organic phase is then preferably washed with brine, concentrated and dried in vacuo.

Another aspect of the invention relates to a product obtainable by, or obtained by, the above-described processes.

Therapeutic Use

Previous studies have shown that VSN16 is an agonist at a novel cannabinoid receptor of the vasculature. It acts on the endothelium to release nitric oxide and activate KCa and TRPV1 (P. M. Hoi, C. Visintin, M. Okuyama, S. M. Gardiner, T. Bennett, D. Baker, D. L. Selwood and C. R. Hiley; *British Journal of Pharmacology,* 2007, 2007, 152, 751-764). Studies have shown that VSN16 relaxes mesenteric arteries in an endothelium-dependent manner. The vasorelaxation is antagonized by high concentrations of the classical cannabinoid antagonists, rimonabant and AM 251, as well as by O-1918, an antagonist at the abnormal-cannabidiol receptor but not at CB1 or CB2 receptors. It does not affect [$^3$H]CP55,940 binding to CB1 receptors in rat cerebellum. The vasorelaxation is not pertussis toxin-sensitive but is reduced by inhibition of nitric oxide synthesis, $Ca^{2+}$-sensitive $K^+$ channels (KCa) and TRPV1 receptors. In conscious rats, VSN16 transiently increases blood pressure and causes a longer-lasting increase in mesenteric vascular conductance. Structure-activity studies on vasorelaxation show a stringent interaction with the target receptor.

VSN16 is therefore believed to be of use in the treatment of prevention or treatment of a muscular disorder, a gastrointestinal disorder, or for treating or controlling spasticity and tremors. See WO 2005/080316 for further details.

Thus, one aspect of the invention relates to a crystalline form as described above for use in medicine.

Yet another aspect of the invention relates to a crystalline form as described above for use in the prevention or treatment of a muscular disorder, a gastrointestinal disorder, or for treating or controlling spasticity and tremors.

Another aspect of the invention relates to the use of a crystalline form as described above in the preparation of a medicament for the prevention or treatment of a muscular disorder, a gastrointestinal disorder, or for treating or controlling spasticity and tremors.

Another aspect of the invention relates to a method for the prevention or treatment of a muscular disorder, a gastrointestinal disorder, or for treating or controlling spasticity and tremors, said method comprising administering a pharmacologically effective amount of a crystalline form as described above to a subject in need thereof.

Preferably, the subject is a warm blooded animal, more preferably still, a human.

As used herein the phrase "preparation of a medicament" includes the use of the above described crystalline form directly as the medicament in addition to its use in a screening programme for further active agents or in any stage of the manufacture of such a medicament.

One preferred embodiment relates to the use of a crystalline form according to the invention in the treatment of a muscular disorder, a gastrointestinal disorder, or for treating or controlling spasticity and tremors.

One preferred embodiment relates to the use of a crystalline form according to the invention in the treatment of a muscular disorder.

In one preferred embodiment, the muscular disorder is a neuromuscular disorder.

One preferred embodiment relates to the use of a crystalline form according to the invention in the treatment of a gastrointestinal disorder.

In another preferred embodiment, the gastrointestinal disorder is selected from a gastric ulcer, Crohn's disease, secretory diarroehea and paralytic ileus.

One preferred embodiment relates to the use of a crystalline form according to the invention for treating or controlling spasticity and tremors.

Pharmaceutical Composition

When crystalline forms of the invention are used as a medicament, preferably as an agent for treatment or prevention of proliferative disorders, the crystalline form can be administered alone, or as a mixture of the crystalline form with an appropriate pharmacologically acceptable excipient(s), and/or diluent(s) and/or carrier(s).

Another aspect of the invention therefore relates to a pharmaceutical composition comprising a crystalline form according as described above and a pharmaceutically acceptable diluent, excipient or carrier.

Compositions according to the present invention can be in unit dosage form such as tablets, capsules, granules, powders, syrups, injections, ointments, solutions, suspensions, aerosols, troches or the like for oral, topical or parenteral administration.

The choice of pharmaceutical carrier, excipient or diluent can be selected with regard to the intended route of administration and standard pharmaceutical practice. The pharmaceutical compositions may comprise as, or in addition to, the carrier, excipient or diluent any suitable binder(s), lubricant(s), suspending agent(s), coating agent(s), solubilising agent(s). The pharmaceutical compositions may be for human or animal usage in human and veterinary medicine.

The pharmaceutical compositions can be prepared in a known manner by using additives such as excipients, binding agents, disintegrating agents, lubricating agents, stabilizing agents, corrigents, suspending agents, diluents and solvents.

Examples of such suitable excipients for the various different forms of pharmaceutical compositions described herein may be found in the "Handbook of Pharmaceutical Excipients, $2^{nd}$ Edition, (1994), Edited by A Wade and P J Weller. An example of an excipient includes a sugar derivative such as lactose, sucrose, glucose, mannitol, or sorbitol; a starch derivative such as corn starch, potato starch, alpha-starch, dextrin, carboxy methylstarch; a cellulose derivative such as crystalline cellulose, low-substituted hydroxypropylcellulose, hydroxypropylmethylcellulose, carboxymethylcellulose, calcium carboxymethylcellulose, internal-cross-linked sodium carboxymethylcellulose; acacia; dextran; pullulan; a silicate derivative such as light silicic acid anhydride, synthetic aluminum silicate, magnesium aluminate metasilicate; a phosphate derivative such as calcium phosphate; a carbonate derivative such as calcium carbonate; a sulfate derivative such as calcium sulfate; or the like.

Acceptable carriers or diluents for therapeutic use are well known in the pharmaceutical art, and are described, for example, in Remington's Pharmaceutical Sciences, Mack Publishing Co. (A. R. Gennaro edit. 1985). Examples of suitable carriers include lactose, starch, glucose, methyl cellulose, magnesium stearate, mannitol, sorbitol and the like. Examples of suitable diluents include ethanol, glycerol and water.

An example of a disintegrating agent includes an excipient described hereinbefore, a chemically modified starch or cellulose derivative such as sodium cross-carmellose, sodium carboxymethylstarch, cross-linked polyvinylpyrrolidone or the like.

Preservatives, stabilizers, dyes and even flavoring agents may be provided in the pharmaceutical composition. Examples of preservatives include sodium benzoate, sorbic acid and esters of p-hydroxybenzoic acid. Antioxidants and suspending agents may be also used.

An example of a stabilizing agent includes a para-hydroxybenzoic acid ester derivative such as methylparabene, propylparabene; an alcohol derivative such as chlorobutanol, benzyl alcohol, phenetyl alcohol; benzalkonium chloride; a phenol derivative such as phenol, cresol; thimerosal; acetic anhydride; sorbic acid; or the like. An example of a corrigent includes a sweetening, souring, and flavoring agents or the like all of which are ordinarily used. An example of a solvent includes water, ethanol, glycerin or the like.

Examples of suitable binders include an excipient described hereinbefore; gelatin; polyvinylpyrrolidone; macrogol; or the like, starch, natural sugars such as glucose, anhydrous lactose, free-flow lactose, beta-lactose, corn sweeteners, natural and synthetic gums, such as acacia, tragacanth or sodium alginate, carboxymethyl cellulose and polyethylene glycol.

An example of a lubricating agent includes talc; stearic acid; a metal stearate derivative such as calcium stearate, magnesium stearate, sodium stearate; colloidal silica; veegum; a wax such as beeswax or spermaceti; boric acid; a glycol; a carboxy acid derivative such as fumaric acid, adipic acid; a sodium carboxylate such as sodium benzoate; a sulfate such as sodium sulfate; leucine; a lauryl sulfate such as sodium lauryl sulfate, or magnesium lauryl sulfate; a silicic acid derivative such as silicic acid anhydride, silicic acid hydrate; a starch derivative described above as an excipient; sodium oleate, sodium acetate, sodium chloride, or the like.

Administration

The pharmaceutical compositions of the present invention may be adapted for oral, rectal, vaginal, parenteral, intramuscular, intraperitoneal, intraarterial, intrathecal, intrabronchial, subcutaneous, intradermal, intravenous, nasal, buccal or sublingual routes of administration.

For oral administration, particular use is made of compressed tablets, pills, tablets, gellules, drops, and capsules. Preferably, these compositions contain from 1 to 250 mg and more preferably from 10-100 mg, of active ingredient per dose.

Other forms of administration comprise solutions or emulsions which may be injected intravenously, intraarterially, intrathecally, subcutaneously, intradermally, intraperitoneally or intramuscularly, and which are prepared from sterile or sterilisable solutions. The pharmaceutical compositions of the present invention may also be in form of suppositories, pessaries, suspensions, emulsions, lotions, ointments, creams, gels, sprays, solutions or dusting powders.

An alternative means of transdermal administration is by use of a skin patch. For example, the active ingredient can be incorporated into a cream consisting of an aqueous emulsion of polyethylene glycols or liquid paraffin. The active ingredient can also be incorporated, at a concentration of between 1 and 10% by weight, into an ointment consisting of a white wax or white soft paraffin base together with such stabilisers and preservatives as may be required.

Injectable forms may contain between 10-1000 mg, preferably between 10-250 mg, of active ingredient per dose.

Compositions may be formulated in unit dosage form, i.e., in the form of discrete portions containing a unit dose, or a multiple or sub-unit of a unit dose.

Dosage

The dose of the crystalline form of the compound will depend on such factors as symptom, body weight and age of the patient. A suitable dosage level is 0.1 mg (preferably 1 mg) per day to 100 mg (preferably 50 mg) per day. The crystalline form of the compound of the invention can be administered as either a single unit dosage, or if desired, the dosage may be divided into convenient subunits administered at one to several times throughout the day depending on the symptoms of the patient.

A person of ordinary skill in the art can easily determine an appropriate dose of one of the instant compositions to administer to a subject without undue experimentation. Typically, a physician will determine the actual dosage which will be most suitable for an individual patient and it will depend on a variety of factors including the activity of the specific compound employed, the metabolic stability and length of action of that compound, the age, body weight, general health, sex, diet, mode and time of administration, rate of excretion, drug combination, the severity of the particular condition, and the individual undergoing therapy. The dosages disclosed herein are exemplary of the average case. There can of course be individual instances where higher or lower dosage ranges are merited, and such are within the scope of this invention.

Combinations

In a particularly preferred embodiment, a crystalline form according to the invention is administered in combination with one or more other pharmaceutically active agents. In such cases, the crystalline form according to the invention may be administered consecutively, simultaneously or sequentially with the one or more other pharmaceutically active agents.

The present invention is further described with reference to the following figures, wherein:

FIG. 1 shows the X-ray powder diffraction pattern of sample VSN16R (needles grown from oil). The diffraction pattern was obtained by irradiation of the crystalline product using a Panalytical X'pert pro diffractometer using Cu K alpha X-ray source 40 Kv and 40 mA. Sample were mounted on silicon wafers due to the small amount of sample. The sample was rotated during analysis to limit orientation effects.

Figure 1:
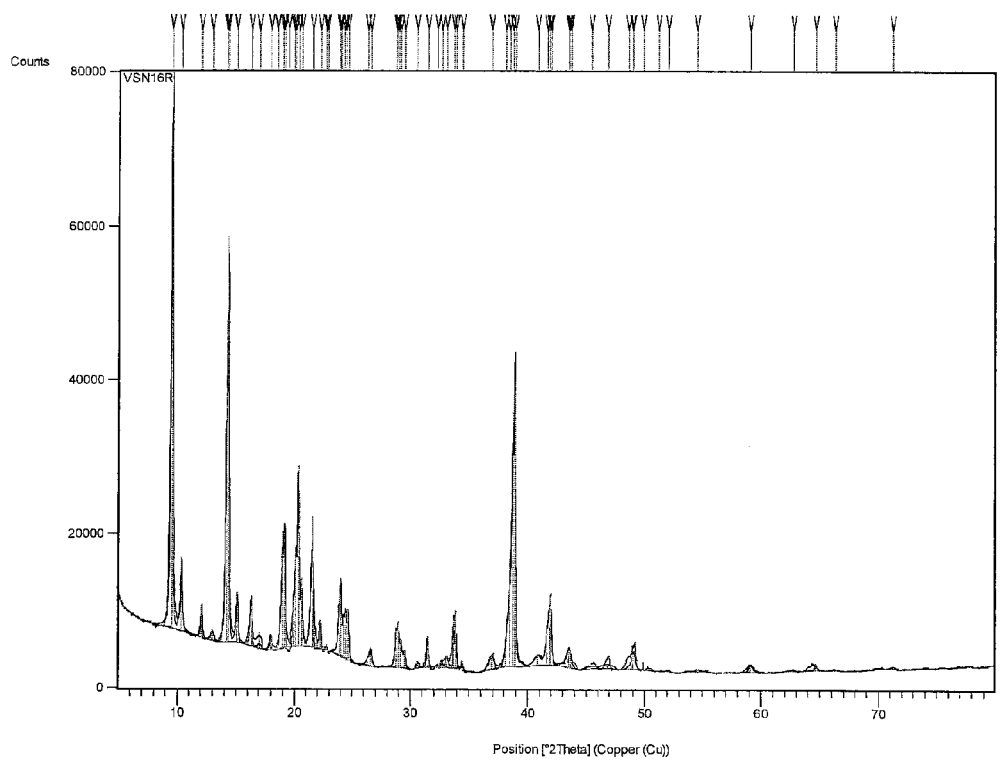

The present invention is further described by non-limiting example.

EXAMPLES

Preparation of Compound

The compound VSN16R is prepared in accordance with the methodology described in WO 2005/080316 (in the name of University College London), WO 2005/080316 (UCL Business PLC) or P. M. Hoi, C. Visintin, M. Okuyama, S. M. Gardiner, T. Bennett, D. Baker, D. L. Selwood and C. R. Hiley; *British Journal of Pharmacology*, 2007, 2007, 152, 751-764.

Method A: Isolation from Oil

VSN16R (1 g) was prepared by the methodology described in WO 2005/080316 or WO 2005/080316 and isolated as an oil. The oil was dried on a rotary evaporator to remove traces of other solvents. Ethyl acetate (100 mL) was added and the solvent removed on a rotary evaporator. This process was repeated twice. The resultant oil in a 100 mL round bottomed flask was scratched with a glass rod and the oil left at room temperature for 1 week. During this time small crystals started to appear which when mixed with the oil induced the bulk material to crystallise. Seeding other batches of oil with a few crystals was sufficient to induce crystallisation. Methyl acetate was also found to be a suitable solvent.

Method B: Crystallisation from Methyl Acetate

VSN16R (2.5 g) was prepared by the methodology described in WO 2005/080316 or WO2005/080316 and isolated as an oil. The oil was dissolved in methyl acetate or ethyl acetate and crystallised as an off white solid.

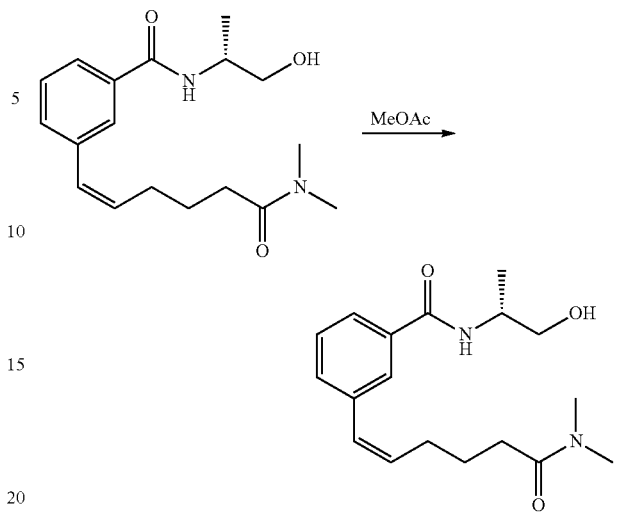

The material was treated with methyl acetate (3.2 vol), warmed to 50° C. to obtain a homogeneous solution, filtered through GF/F microfibre filter paper (filtration to remove traces of palladium and solids) and then cooled to 5° C., seeded (0.1 wt %) and upon visible growth cooled to 0° C. and stirred for 1 hour, filtered and washed with cold methyl acetate to give (225 g), then and dried in vacuum oven at 25° C. until constant mass (200 g). HPLC analysis indicated an impurity at 10%. The material was dissolved in dichloromethane (1 L, 5 vol) and washed with 1 m HCl (2×0.5 L and then brine (0.5 L) and concentrated to give a clear oil (197 g). The material was dissolved in methyl acetate (0.63 L, 3.2 vol), filtered and charged to vessel. The solution was warmed to 50° C. and then cooled to 5° C. and seeded (0.15 g, 0.075 wt %) and stirred until visible growth. The temperature was adjusted to 0° C. and left to stir for 1 h then filtered washed with methyl acetate (150 ml, 0.75 vol) to give (147 g), placed in vacuum oven at 25° C. until at constant mass (144 g, 60% overall).

Measurement Conditions:

1. X-Ray Powder Diffraction Studies (XRPD)

Two samples of crystalline material were submitted for XRPD analysis using a using a Panalytical X'pert pro diffractometer using Cu K alpha X-ray source 40 Kv and 40 mA. Samples were mounted on silicon wafers due to the small amount of sample. The sample was rotated during analysis to limit orientation effects.

The sample was irradiated with Cu Kα radiation (40 kV, 40 mA). The samples chosen were the reference VSN16R needles (prepared by Method A) and the crystalline solid isolated using methyl acetate (VP1218-59-42; prepared by Method B).

| | |
|---|---|
| Comment | Configuration = Transmission Spinner Stage, Goniometer = PW3050/60 (Theta/Theta); Minimum step size 2Theta: 0.001; Minimum step size Omega: 0.001 Sample stage = Transmission Spinner PW3064/60; Minimum step size Phi: 0.1 Diffractometer system = XPERT-PRO Measurement program = Single experiment Si wafer polymer 10-80 1 hour minutes run |
| Raw Data Origin | XRD measurement (*.XRDML) |
| Scan Axis | Gonio |
| Start Position [°2Th.] | 5.0084 |

-continued

| | |
|---|---|
| End Position [°2Th.] | 79.9784 |
| Step Size [°2Th.] | 0.0170 |
| Scan Step Time [s] | 30.3660 |
| Scan Type | Continuous |
| PSD Mode | Scanning |
| PSD Length [°2Th.] | 2.12 |
| Offset [°2Th.] | 0.0000 |
| Divergence Slit Type | Fixed |
| Divergence Slit Size [°] | 1.0000 |
| Specimen Length [mm] | 10.00 |
| Measurement Temp [° C.] | 25.00 |
| Anode Material | Cu |
| K-Alpha1 [Å] | 1.54060 |
| K-Alpha2 [Å] | 1.54443 |
| K-Beta [Å] | 1.39225 |
| K-A2/K-A1 Ratio | 0.50000 |
| Generator Settings | 40 mA, 40 kV |
| Diffractometer Type | 0000000011025943 |
| Diffractometer Number | 0 |
| Goniometer Radius [mm] | 240.00 |
| Dist. Focus-Diverg. Slit [mm] | 100.00 |
| Incident Beam Monochromator | No |
| Spinning | Yes |

The XRPD results show that the solids isolated from methods A and B are the same polymorph. The XRPD trace for VSN16R is shown in FIG. 1. Peak values and their relative intensities are listed in Table 1.

Comparison of the diffractograms for VSN16R and VP1218-59-42 indicate that the materials are the same polymorph. The same peaks were present in both of the samples with only a slight shift in position as a result of sample height displacement or slight variations in d-spacings between the planes. Minor differences in peak intensity and shape are most likely attributable to differences in the sample morphology and crystallite size. VSN16R is more crystalline and given the sharp narrow peaks is indicative of larger crystallites. The peaks for sample VP1218-59-42 were slightly broader, indicating low crystallinity/smaller crystallite size. VSN16R show reflections from what appears to be a second phase or impurity (additional peaks at ca 28°2) that is not present in VP1218-59-42 sample.

2. Microscopy

Figure 2:
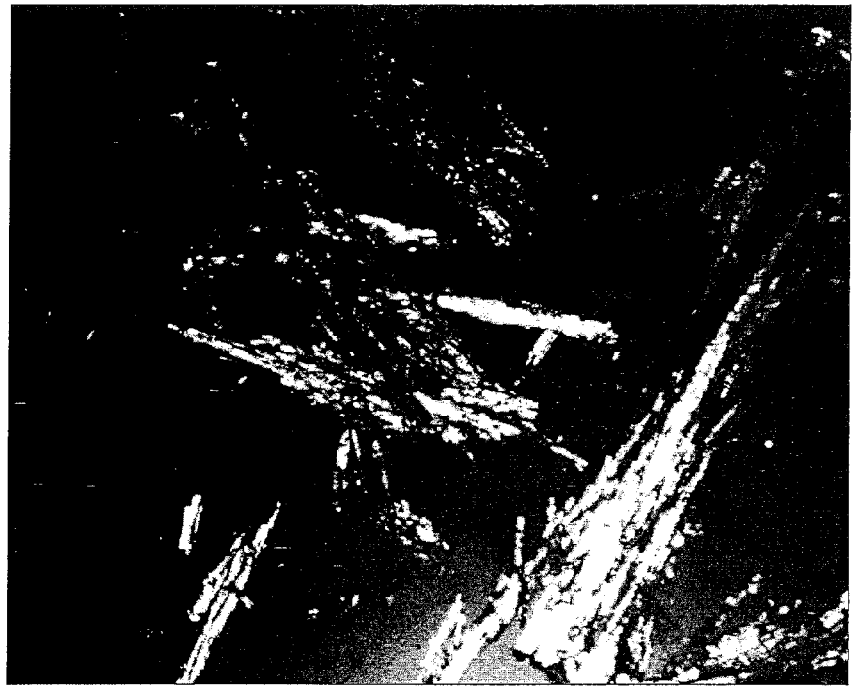
FIG. 2 shows crystals of sample VSN16R (needles grown from oil) using a Leitz Laborlux 12, hot stage, polarised light microscope. Objective Nikon 4, 0.1, 160/-.
Figure 3:
FIG. 3 shows crystals of sample VP1218-58-42 (obtained from methyl acetate recrystallisation carried out on a 2.5 g scale) using a using a Leitz Laborlux 12, hot stage, polarised light microscope. Objective Nikon 4, 0.1, 160/-.
Figure 4:
FIG. 4 shows crystals of sample VP1218-48-100F3 using a using a Leitz Laborlux 12, hot stage, polarised light microscope. Objective Nikon 4, 0.1, 160/-.

Microscopy studies were carried out using a polarised light source to compare morphology of the crystals and assess the level of crystallinity. Microscopy studies showed that the crystalline solids isolated are small needles and aggregates thereof. Studies were carried out using a Leitz Laborlux 12, hot stage, polarised light microscope. Objective Nikon 4, 0.1, 160/-. The solids from samples VSN16R (Method A—needles grown from the oil), VP1218-58-42 (Method B—methyl acetate recrystallisation carried out on a 2.5 g scale) and VP1218-48-100F3 (prepared in block C of the crystallisation trials using hexane solvent) are illustrated in FIGS. 2, 3 and 4 respectively, and show a needle morphology.

Various modifications and variations of the described methods of the invention will be apparent to those skilled in the art without departing from the scope and spirit of the invention. Although the invention has been described in connection with specific preferred embodiments, various modifications of the described modes for carrying out the invention which are obvious to those skilled in chemistry or related fields are intended to be within the scope of the following claims.

TABLE 1

XRD data for crystalline compound (Ia) prepared in accordance with the invention

| Pos. [°2Th.] | Height [cts] | FWHM [°2Th.] | d-spacing [Å] | Rel. Int. [%] |
|---|---|---|---|---|
| 9.5294 | 72183.36 | 0.1391 | 9.27362 | 100.00 |
| 10.3494 | 9525.68 | 0.1223 | 8.54056 | 13.20 |
| 12.0641 | 4214.64 | 0.1123 | 7.33023 | 5.84 |
| 12.9497 | 1486.64 | 0.2045 | 6.83088 | 2.06 |
| 14.2062 | 33376.89 | 0.1550 | 6.22942 | 46.24 |
| 14.3484 | 52805.83 | 0.0826 | 6.16801 | 73.16 |
| 15.1066 | 6518.39 | 0.1533 | 5.86010 | 9.03 |
| 16.3406 | 6427.79 | 0.1619 | 5.42021 | 8.90 |
| 17.0613 | 1896.43 | 0.4098 | 5.19286 | 2.63 |
| 17.9788 | 1993.55 | 0.1550 | 4.92987 | 2.76 |
| 18.5470 | 732.22 | 2.7778 | 4.78009 | 1.01 |
| 19.0220 | 15149.23 | 0.2171 | 4.66178 | 20.99 |
| 19.1771 | 15169.67 | 0.0312 | 4.62443 | 21.02 |
| 19.4820 | 845.60 | 0.0694 | 4.55274 | 1.17 |
| 19.9328 | 5916.73 | 0.2613 | 4.45079 | 8.20 |
| 20.1116 | 12167.39 | 0.1259 | 4.41161 | 16.86 |
| 20.3397 | 23429.01 | 0.1291 | 4.36265 | 32.46 |
| 20.6273 | 8379.38 | 0.1108 | 4.30246 | 11.61 |
| 21.5525 | 16917.65 | 0.2177 | 4.12323 | 23.44 |
| 22.2402 | 3559.00 | 0.1055 | 3.99396 | 4.93 |
| 22.7529 | 34.57 | 2.7778 | 3.90510 | 0.05 |
| 22.8480 | 34.51 | 0.0694 | 3.88906 | 0.05 |
| 23.9060 | 8158.17 | 0.2052 | 3.71929 | 11.30 |
| 24.0333 | 9656.44 | 0.0577 | 3.69987 | 13.38 |
| 24.2616 | 5642.61 | 0.1141 | 3.66558 | 7.82 |
| 24.4328 | 6156.90 | 0.1061 | 3.64028 | 8.53 |
| 24.6339 | 6530.60 | 0.0990 | 3.61101 | 9.05 |
| 26.3586 | 1096.59 | 0.2617 | 3.37852 | 1.52 |
| 26.5828 | 2363.22 | 0.1379 | 3.35053 | 3.27 |
| 28.7484 | 4804.55 | 0.1461 | 3.10287 | 6.66 |
| 28.8428 | 4946.35 | 0.2282 | 3.09293 | 6.85 |
| 28.9388 | 5859.59 | 0.0536 | 3.08289 | 8.12 |
| 29.1704 | 3587.83 | 0.2203 | 3.05893 | 4.97 |
| 29.5031 | 2460.81 | 0.0984 | 3.02520 | 3.41 |
| 30.5236 | 722.45 | 0.1045 | 2.92633 | 1.00 |
| 31.4477 | 3950.16 | 0.0929 | 2.84242 | 5.47 |
| 32.2912 | 365.85 | 0.1045 | 2.77007 | 0.51 |
| 32.6825 | 930.40 | 0.0813 | 2.73779 | 1.29 |
| 33.1202 | 1391.99 | 0.1626 | 2.70260 | 1.93 |
| 33.7176 | 6350.10 | 0.0425 | 2.65608 | 8.80 |
| 33.8883 | 7452.23 | 0.0697 | 2.64308 | 10.32 |
| 34.4214 | 1277.13 | 0.0697 | 2.60336 | 1.77 |
| 36.8861 | 1713.76 | 0.3368 | 2.43487 | 2.37 |
| 38.0790 | 2453.82 | 0.9581 | 2.36129 | 3.40 |
| 38.4750 | 11144.07 | 0.2996 | 2.33789 | 15.44 |
| 38.7056 | 32806.34 | 0.1481 | 2.32449 | 45.45 |
| 38.8873 | 37072.42 | 0.0913 | 2.31405 | 51.36 |
| 40.8219 | 1388.37 | 0.5550 | 2.20874 | 1.92 |
| 41.6544 | 4835.27 | 0.2198 | 2.16650 | 6.70 |
| 41.8320 | 7667.92 | 0.1227 | 2.15771 | 10.62 |
| 41.9496 | 8857.88 | 0.0820 | 2.15193 | 12.27 |
| 43.4664 | 2538.68 | 0.3881 | 2.08029 | 3.52 |
| 43.5109 | 2636.15 | 0.2688 | 2.07826 | 3.65 |
| 43.6560 | 1990.96 | 0.7647 | 2.07169 | 2.76 |
| 45.3900 | 408.12 | 2.3980 | 1.99650 | 0.57 |
| 46.8349 | 651.93 | 1.3106 | 1.93821 | 0.90 |
| 48.6124 | 528.05 | 0.1455 | 1.87142 | 0.73 |
| 48.9405 | 2028.06 | 0.1719 | 1.85963 | 2.81 |
| 49.0426 | 2465.56 | 0.1789 | 1.85600 | 3.42 |
| 49.8870 | 52.60 | 0.0694 | 1.82654 | 0.07 |
| 51.1822 | 33.40 | 2.7778 | 1.78332 | 0.05 |
| 52.0528 | 295.52 | 0.1859 | 1.75553 | 0.41 |
| 54.5168 | 285.16 | 0.2323 | 1.68186 | 0.40 |
| 59.0934 | 932.12 | 0.2323 | 1.56205 | 1.29 |
| 62.7309 | 316.28 | 0.1394 | 1.47994 | 0.44 |
| 64.6325 | 820.55 | 0.1162 | 1.44091 | 1.14 |
| 66.2897 | 146.93 | 0.2788 | 1.40885 | 0.20 |
| 71.2040 | 251.66 | 0.3400 | 1.32319 | 0.35 |

The invention claimed is:

1. A crystalline form of a compound of formula I(a),

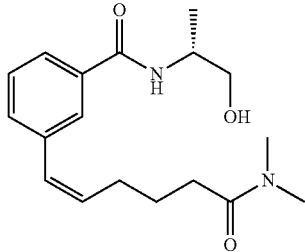

(Ia)

which is characterized by an x-ray powder diffraction pattern having at least two diffraction peaks selected from the following 2 theta values: 9.53±0.3, 10.35±0.3, 14.21±0.3, 14.35±0.3, 19.02±0.3, 19.18±0.3, 20.11±0.3, 20.34±0.3, 20.63±0.3, 21.55±0.3, 23.91±0.3, 24.03±0.3, 33.89±0.3, 38.48±0.3, 38.71±0.3, 38.89±0.3, 41.83±0.3 and 41.95±0.3.

2. A crystalline form of a compound of formula I(a),

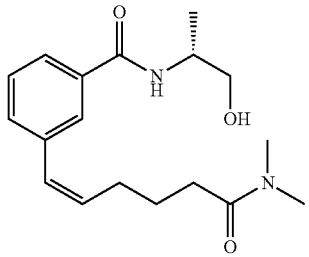

(Ia)

which is characterized by an x-ray powder diffraction pattern having at least two diffraction peaks selected from the following 2 theta values: 9.53±0.3, 14.21±0.3, 14.35±0.3, 19.02±0.3, 19.18±0.3, 20.34±0.3, 21.55±0.3, 38.71±0.3 and 38.89±0.3.

3. A crystalline form of a compound of formula I(a),

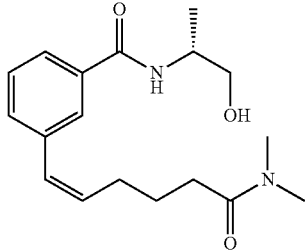

(Ia)

which is characterized by an x-ray powder diffraction pattern having at least two diffraction peaks selected from the following 2 theta values: 9.53±0.3, 14.21±0.3, 14.35±0.3, 38.71±0.3 and 38.89±0.3.

4. A crystalline form of a compound of formula I(a),

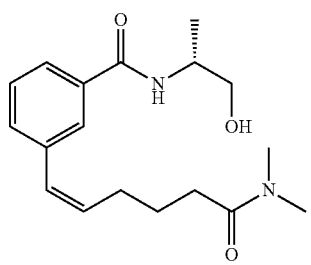

(Ia)

which is characterized by an x-ray powder diffraction pattern having at least three diffraction peaks selected from the following 2 theta values: 9.53±0.3, 14.21±0.3, 14.35±0.3, 38.71±0.3 and 38.89±0.3.

5. A crystalline form of a compound of formula I(a),

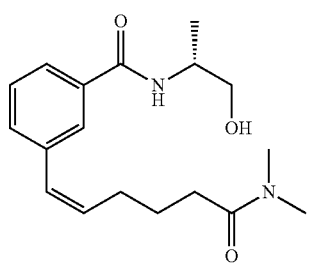

(Ia)

which is characterized by an x-ray powder diffraction pattern having at least four diffraction peaks selected from the following 2 theta values: 9.53±0.3, 14.21±0.3, 14.35±0.3, 38.71±0.3 and 38.89±0.3.

6. A crystalline form of a compound of formula I(a),

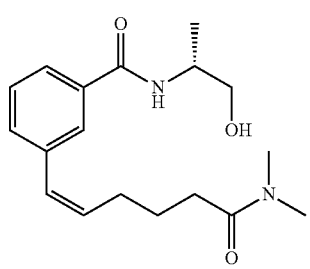

(Ia)

which is characterized by an x-ray powder diffraction pattern having all five diffraction peaks selected from the following 2[theta] values: 9.53±0.3, 14.21±0.3, 14.35±0.3, 38.71±0.3 and 38.89±0.3.

7. A crystalline form of a compound of formula I, which is characterized by an x-ray powder diffraction pattern having peak positions selected from the following 2 theta values: 9.5294, 10.3494, 12.0641, 12.9497, 14.2062, 14.3484, 15.1066, 16.3406, 17.0613, 17.9788, 19.0220, 19.1771, 19.9328, 20.1116, 20.3397, 20.6273, 21.5525, 22.2402, 23.9060, 24.0333, 24.2616, 24.4328, 24.6339, 26.5828, 28.7484, 28.8428, 28.9388, 29.1704, 29.5031, 31.4477, 33.7176, 33.8883, 36.8861, 38.0790, 38.4750, 38.7056, 38.8873, 41.6544, 41.8320, 41.9496, 43.4664, 43.5109, 43.6560, 48.9405 and 49.0426

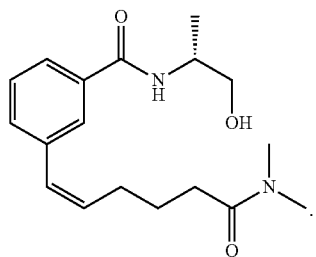
(I)
* * * * *